(12) United States Patent
Stentiford

(10) Patent No.: US 10,632,270 B2
(45) Date of Patent: Apr. 28, 2020

(54) THERAPEUTIC TREATMENT METHODS AND APPARATUS FOR USE THEREIN

(71) Applicant: SOE Health Limited, Beeston, Nottingham (GB)

(72) Inventor: Neil Stentiford, Nottingham (GB)

(73) Assignee: SOE Health Limited, Beeston, Nottingham (GB)

( * ) Notice: Subject to any disclaimer, the term of this patent is extended or adjusted under 35 U.S.C. 154(b) by 327 days.

(21) Appl. No.: 15/541,351

(22) PCT Filed: Jan. 13, 2016

(86) PCT No.: PCT/GB2016/000006
§ 371 (c)(1),
(2) Date: Jun. 30, 2017

(87) PCT Pub. No.: WO2016/113535
PCT Pub. Date: Jul. 21, 2016

(65) Prior Publication Data
US 2018/0021531 A1    Jan. 25, 2018

(30) Foreign Application Priority Data
Jan. 13, 2015  (GB) .................. 1500512.7

(51) Int. Cl.
*A61M 15/02*     (2006.01)
*A61N 5/06*      (2006.01)
*C01B 13/02*     (2006.01)

(52) U.S. Cl.
CPC ............. *A61M 15/02* (2013.01); *A61N 5/062* (2013.01); *C01B 13/0248* (2013.01);
(Continued)

(58) Field of Classification Search
CPC ... A61B 5/08; A61B 5/14542; A61B 5/14551; A61K 2300/00; A61K 31/197;
(Continued)

(56) References Cited

U.S. PATENT DOCUMENTS 5,396,882 A * 3/1995 Zapol .................... A61M 15/02
128/200.14
6,314,956 B1 * 11/2001 Stamler ................. A61K 31/197
128/200.24

(Continued)

FOREIGN PATENT DOCUMENTS

| WO | 9729044 A1 | 8/1997 |
| WO | 0117596 A1 | 3/2001 |

(Continued)

OTHER PUBLICATIONS

ScienceDirect, "Phthalocyanine"—excerpt from: Peter A. Lewis, "Colored Organic Pigments" in Applied Polymer Science: 21st Century, 2000. Accessed Dec. 2, 2019 (Year: 2000).*

*Primary Examiner* — Annette Dixon
(74) *Attorney, Agent, or Firm* — Young Basile Hanlon & MacFarlane, P.C.

(57) ABSTRACT

A method of treating a subject suffering from, or susceptible to, a condition that can be ameliorated by inhalation of gaseous nitrite comprises the use of an apparatus comprising an activating unit that includes a photosensitiser excitable by absorption of light to excite oxygen to a singlet state, and a light source arranged to illuminate the photosensitiser. Air is caused to flow through the activating unit while the photosensitiser is illuminated by the light source, and after passing through the activating unit, is directed to the respiratory tract of the subject.

7 Claims, 5 Drawing Sheets

(52) U.S. Cl.
CPC ............... *A61M 2202/0275* (2013.01); *A61N 2005/0604* (2013.01); *A61N 2005/0651* (2013.01)

(58) Field of Classification Search
CPC .... A61K 31/21; A61K 31/407; A61K 31/421; A61K 31/4965; A61K 31/65; A61K 33/00; A61K 33/04; A61K 33/24; A61K 33/30; A61K 33/34; A61K 38/482; A61K 41/0019; A61K 41/0057; A61K 45/06; A61K 9/007; A61K 9/12; A61K 9/14; A61K 9/2031; A61K 9/205; A61K 9/7007; A61K 31/00; A61K 31/28; A61K 31/555; A61K 31/60; A61K 31/603; A61K 31/695; A61K 31/7048; A61K 31/7135; A61K 33/14; A61K 33/32; A61K 35/18; A61K 41/0071; A61K 47/52; A61L 2/0005; A61L 2/0011; A61L 2/0082; A61L 2/0088; A61L 2/02; A61L 2/08; A61L 2/088; A61L 2/10; A61L 2/16; A61L 2/0047; A61L 2/0076; A61L 2/24; A61L 2/26; A61L 2202/14; A61L 2202/22; A61M 1/0272; A61M 1/3681; A61M 1/3683; A61M 11/002; A61M 11/003; A61M 11/005; A61M 11/06; A61M 15/00; A61M 15/0016; A61M 15/0085; A61M 15/0086; A61M 15/02; A61M 15/025; A61M 16/0051; A61M 16/0057; A61M 16/024; A61M 16/0666; A61M 16/0672; A61M 16/085; A61M 16/10; A61M 16/107; A61M 16/1075; A61M 16/12; A61M 16/122; A61M 16/14; A61M 16/202; A61M 16/208; A61M 2016/0027; A61M 2016/0039; A61M 2016/1025; A61M 2016/1035; A61M 2202/0275; A61M 2205/18; A61M 2205/33; A61M 2205/3553; A61M 2205/3561; A61M 2205/3592; A61M 2205/505; A61M 2205/52; A61M 2206/14; A61M 2206/16; A61M 2209/06; A61M 2230/205; B01D 53/46; B01D 53/56; C01B 21/24; C12N 15/113; C12N 2310/14; C12N 5/0641; C12N 13/00; C12Y 304/21075; G01N 33/0037; Y02A 50/245; Y02A 50/385; Y10T 436/12; C07F 11/005; C07F 13/005; C07F 15/02; C07F 17/00

See application file for complete search history.

(56) References Cited

U.S. PATENT DOCUMENTS

| | | | | |
|---|---|---|---|---|
| 6,692,694 | B1* | 2/2004 | Curry | A61L 2/088 |
| | | | | 422/1 |
| 6,843,961 | B2* | 1/2005 | Hlavinka | A61K 31/00 |
| | | | | 422/1 |
| 7,897,399 | B2* | 3/2011 | Hyde | G01N 33/0037 |
| | | | | 436/55 |
| 8,339,592 | B2* | 12/2012 | Hlavinka | A61L 2/0011 |
| | | | | 356/216 |
| 9,044,523 | B2* | 6/2015 | Hlavinka | A61K 41/0019 |
| 2001/0037810 | A1* | 11/2001 | Fine | A61K 33/00 |
| | | | | 128/203.26 |
| 2002/0015662 | A1* | 2/2002 | Hlavinka | A61L 2/0076 |
| | | | | 422/24 |
| 2003/0062043 | A1* | 4/2003 | Fine | A61K 9/007 |
| | | | | 128/203.12 |
| 2003/0228564 | A1* | 12/2003 | Edrich | A61K 41/0019 |
| | | | | 435/2 |
| 2004/0058101 | A1 | 3/2004 | Klemm | |
| 2004/0086559 | A1 | 5/2004 | Peters et al. | |
| 2006/0180147 | A1* | 8/2006 | Rounbehler | A61M 16/10 |
| | | | | 128/203.12 |
| 2012/0100039 | A1* | 4/2012 | Appeaning | A61L 2/088 |
| | | | | 422/22 |
| 2014/0109899 | A1* | 4/2014 | Boucher | A61M 11/06 |
| | | | | 128/200.18 |
| 2014/0275901 | A1* | 9/2014 | Flanagan | A61B 5/14542 |
| | | | | 600/364 |

FOREIGN PATENT DOCUMENTS

| | | |
|---|---|---|
| WO | 2012034089 A1 | 3/2012 |
| WO | 2012056225 A1 | 5/2012 |
| WO | 2013181179 A1 | 12/2013 |

\* cited by examiner

THERAPEUTIC TREATMENT METHODS AND APPARATUS FOR USE THEREIN

CROSS REFERENCE TO RELATED APPLICATION

The present application is a 371 of International Patent Application No. PCT/GB2016/000006, filed Jan. 13, 2016, which claims priority to Great Britain Patent Application No. 1500512.7, filed Jan. 13, 2015, each incorporated herein in its entirety.

TECHNICAL FIELD

This invention relates to methods of treating conditions that can be ameliorated by inhalation of gaseous nitrite. In particular, the invention relates to the use of apparatus of the type used to produce singlet oxygen energy. The invention further relates to improvements in such apparatus.

BACKGROUND

Singlet oxygen is a reactive energetic form of oxygen which can be formed naturally by the interaction of electromagnetic radiation with atmospheric oxygen, singlet oxygen energy being released when the singlet oxygen molecule returns to the stable, or ground state.

It is well-known to artificially produce singlet oxygen using photosensitisers, which are compounds such as dyes that initiate a photochemical reaction. To produce singlet oxygen, a photosensitiser is excited by light radiation and subsequent excitonic hits between oxygen molecules and the excited photosensitiser cause the oxygen molecule to become excited from the ground triplet state to the singlet state.

Various therapeutic benefits have been attributed to the administration of singlet oxygen to a patient, and apparatus for producing singlet oxygen is known in the prior art. One such apparatus is described in our earlier patent application WO2012/056225. That apparatus comprises an activating unit through which atmospheric air is caused to flow, the activating unit comprising at least one light-emitting diode (LED) light source and at least part of a wall of the activating unit being coated with a photosensitiser. Irradiation of the photosensitiser by the LED causes some oxygen molecules in the flow of air through the activating unit to adopt the singlet oxygen state. Upon exiting the apparatus, these molecules return to the stable ground state, releasing the acquired energy into the air, which is inhaled by a patient. Typically, such a device may be used in the room in which the patient sleeps, providing a steady supply of energised oxygen.

It has now been found that apparatus of the type described above, which has previously been used to for the generation of singlet oxygen, also results in the delivery to the patient of gaseous nitrite. The apparatus may therefore be used for the treatment of conditions that may be ameliorated by the inhalation of air that contains gaseous nitrite.

SUMMARY

Thus, according to a first aspect of the invention, there is provided a method of treating a subject suffering from, or susceptible to, a condition that can be ameliorated by inhalation of gaseous nitrite, which method comprises
a) providing apparatus comprising an activating unit that includes a photosensitiser excitable by absorption of light to excite oxygen to a singlet state, and a light source arranged to illuminate the photosensitiser;
b) causing air to flow through the activating unit while said photosensitiser is illuminated by the light source; and
c) directing said air, after passage of the air through the activating unit, to the respiratory tract of the subject.

In another aspect of the invention, there is provided apparatus including an activating unit that includes a photosensitiser excitable by absorption of light to excite oxygen to a singlet state and the activating unit further comprising a light source arranged to illuminate the photosensitiser, for use in the treatment of a condition that can be ameliorated by inhalation of gaseous nitrite.

Without wishing to be bound by theory, it is believed that the invention involves the delivery of gaseous nitrite to the body via the lungs, a novel route of delivery, in contrast to the normal route, which is through the digestive system. The inhaled gaseous nitrite enters the accepted Nitrogen Cycle—nitrate>nitrite>NO—and becomes an additional source of NO for the body. The gaseous nitrite dissolves in water, crosses the pulmonary capillary bed, and is transported around the blood system by the haemoglobin. Thus, the body obtains a steady supply of nitrite, and hence NO, that may have a number of beneficial effects, as set out below.

Nitrite ions ($NO_2^-$) are known to occur in bodily fluids, and drugs containing, or constituting sources of, nitrite have been widely used in medicine for some time, to treat various conditions. Nitrite is crucially a precursor to NO (nitrous oxide), which is now known to be a signalling molecule in the cardiovascular system.

Nitrite is known to act as a vasodilator. Thus, in one embodiment of the present invention, the condition that is treated is one that is characterised by vasoconstriction, for instance angina or hypertension.

The role of NO in the cardiovascular system involves that molecule binding to guanylate cyclase receptors, which results in increased levels of cyclic guanosine monophosphate (cGMP), leading to smooth muscle relaxation (vasodilation).

Drugs such as sildenafil used in the treatment of erectile dysfunction act by protecting cGMP from degradation by cGMP-specific enzymes (phosphodiesterase type 5) in the corpus cavernosum of the penis. The resulting smooth muscle relaxation of the intimal cushions of the helicine arteries leads to vasodilation and increased inflow of blood into the spongy tissue of the penis, causing an erection. Increased concentration of NO, which may be derived from inhaled nitrite, may have a similar effect. Thus, the method of the present invention may be effective in the treatment of erectile dysfunction.

Nitrite has also been used in the treatment of epilepsy, though the large doses used and the formation of carcinogenic nitrosamines in the stomach following ingestion of such large doses led to disapproval of such treatment. Inhalation of nitrite, in accordance with the method of the present invention, may overcome problems of that nature. Thus, the method of the invention may be effective in the treatment of epilepsy.

Nitrite is also known to possess anti-microbial, and in particular anti-bacterial, properties. Acidified nitrite is known, for instance, to kill antibiotic-resistant Pseudomonas bacteria. Thus, the method of the invention may be effective in the treatment of bacterial infections of the respiratory tract. Such treatment may be particularly beneficial in relation to the chronic lung infections that occur in patients with cystic fibrosis.

Bio-available gaseous nitrite has been shown to be beneficial to sufferers from chronic obstructive pulmonary disorder (COPD), for various reasons. The gaseous nitrite itself acts as a relaxant in the lungs, improving their elasticity and the ability of oxygen to reach the smallest airways, the alveoli, for transfer into the blood stream. Hence, the method of the invention will improve the blood saturation levels for a COPD sufferer. The steady supply of nitrite, and hence NO, may have a number of beneficial effects in the body, including: vasodilation (relaxation of the blood vessels), enabling better blood flow and more oxygen at the cellular level; better cellular production of ATP; and improved cellular repairs. When the nitrite is converted to NO, it releases oxygen and energy that may be used by the body. Other respiratory disorders that may benefit from the method of the invention include asthma and emphysema.

Gaseous nitrite, which converts to NO in the body, has been shown to be beneficial to sufferers from myalgic encephalomyelitis (ME), chronic fatigue syndrome and fibromyalgia. According to one theory, sufferers from these conditions have endured a bacterial infection of the gut, which dramatically reduces their ability to ingest nitrate and nitrite, leading to a chronic shortage in the body of NO. The delivery of gaseous nitrite overcomes this problem, and the body can recover accordingly.

It is widely acknowledged that NO promotes sleep. Conversely, a deficiency in NO has been shown to be a major contributor to poor sleep, specifically poor rapid eye movement (REM) and slow-wave sleep. Inhalation of nitrite, in accordance with the method of the present invention, may therefore promote sleep and also lead to better quality sleep. The method of the invention may be particularly beneficial for people who suffer from sleep disorders.

The majority of sufferers of Autism Spectrum Disorder (ASD) also suffer from sleep disorders, whether or not they are aware of it. They will generally suffer from increased non-REM and decreased REM sleep and slow-wave sleep, which are the stages of deepest sleep when the body does much of its repair and regenerative work. A general correlation has been found between the extent to which sleep is disordered and the severity of ASD symptoms.

Gaseous nitrite has been found to be beneficial to ASD sufferers and in many cases the benefits are dramatic. While this may be due primarily to improvements in sleep, the benefits are not limited to sleep, and include improvements in cognition, verbal expression, behaviour, alertness and general wellbeing and restfulness. Thus, the method of the present invention may be effective in the treatment of ASD.

The apparatus used in the present invention may be apparatus as described in International Patent Application WO-A-2012/056225. In general, such apparatus will comprise a housing, the activating unit including the photosensitiser and the light source, and a fan arranged to cause air to flow through the activating unit.

The photosensitiser may be a phthalocyanine, such as a green and/or blue phthalocyanine. In a preferred embodiment, the phthalocyanine is a blue phthalocyanine. Other forms of photosensitiser may also be used, for instance methylene blue, rose bengal or a porphyrin.

Preferably, the photosensitiser is coated on a planar substrate. The planar substrate may have the form of a plate or disc. The photosensitiser most commonly has the form of a finely divided powder, and coating of the photosensitiser on the substrate may be carried out be various means. In some cases, an effective coating may be achieved by using a substrate with a roughened or pitted surface and distributing the photosensitiser over that surface such that the particles of photosensitiser are retained within the depressions in the surface of the substrate.

The photosensitiser may be mixed with a powdered or granular adjuvant.

In other cases, coating may be achieved by dispersing the photosensitiser in a curable liquid coating that is applied as a film across the surface of the substrate, and/or by the application of pressure and/or elevated temperature.

The light source is preferably one or, more commonly, more light-emitting diodes (LEDs). Suitable forms of LED include organic LEDs (OLEDs).

Preferably, the LEDs are mounted on an illuminating panel that is spaced apart from, and juxtaposed with, the photosensitiser, such that light from the LEDs impinges upon the photosensitiser. Most commonly, this means that the illuminating panel(s) are spaced apart from, and juxtaposed with, the substrate that is coated with photosensitiser. The illuminating panels are preferably made of, or coated with, a reflective substance to maximise the energy retained within the activating unit.

The gap between the coated substrate and the illuminating panel constitutes a channel through which air is drawn, in use.

In preferred arrangements, the substrate is coated on both sides with photosensitiser and two illuminating panels are provided, one on each side of the coated substrate. Air then flows across both surfaces of the coated substrate, between the substrate and the illuminating panels spaced apart from each of its major surfaces.

The LEDs are preferably surface-mounted on the illuminating panel(s), with the control electronics for the LEDs being mounted on the reverse side of the illuminating panel(s).

The means by which air is caused to flow through the apparatus of the invention may be a conventional electric fan. Most conveniently, the apparatus comprises a substantially enclosed housing, with an inlet through which air is, in use, drawn by the fan and an outlet via which air is emitted from the apparatus after passing through the activating unit.

After prolonged use, the photosensitiser may become less effective. A disadvantage of previous designs of apparatus of the general type described above is that replacement of the photosensitiser is relatively difficult, and normally requires return of the apparatus to the manufacturer or to a remote service site. This results in the user being without the apparatus for a period of several days at least.

This problem is addressed by the present invention, which further provides apparatus for producing singlet oxygen, the apparatus comprising a housing having an air inlet and an air outlet;

a fan arranged within the housing to draw air from the air inlet to the air outlet; and an activating unit disposed in the path of the air from the air inlet to the air outlet, wherein the activating unit includes a photosensitiser excitable by absorption of light to excite oxygen to a singlet state, and a light source arranged to illuminate the photosensitiser;

wherein the photosensitiser is coated on a planar substrate that is mounted on a carriage that, in use, extends through an opening in the housing such that the photosensitiser is positioned within the housing in juxtaposition with the light source, and wherein the carriage can be separated from the housing to permit replacement of the photosensitiser.

The apparatus of this aspect of the invention enables the photosensitiser to be readily replaced. Most importantly, this operation may be carried out by the user of the apparatus, without the need to return the apparatus to the manufacturer or to depatch it to a remote service site, which would leave the user without the apparatus for a period of several days or more. Typically, the user may order a replacement photosensitiser-coated substrate at regular intervals, for instance every three months or every six months, and carry out the replacement himself. The old substrate may be discarded or returned to the manufacturer for recycling.

The carriage most preferably comprises a tray on which the photosensitiser-coated substrate rests. The substrate may be secured to the tray, for instance by means of one or more bolts or other mechanical fixings.

The carriage is most preferably such that when it is inserted into the apparatus it forms part of the housing of the apparatus to form a substantially complete enclosure.

In preferred embodiments, the substrate is coated on both sides with photosensitiser, and the carriage is configured such that substantially all of both major surfaces of the substrate are exposed. In such arrangements, the apparatus generally includes two illuminating panels and the carriage positions the substrate substantially centrally between those panels, so that radiation from one illuminating panel impinges on one surface of the substrate and radiation from the other illuminating panel impinges on the other surface.

DESCRIPTION OF THE DRAWINGS

A preferred embodiment of apparatus according to the present invention will now be described, by way of example only, with reference to the accompanying drawings, in which.

DETAILED DESCRIPTION OF THE EMBODIMENTS

Figure 1:
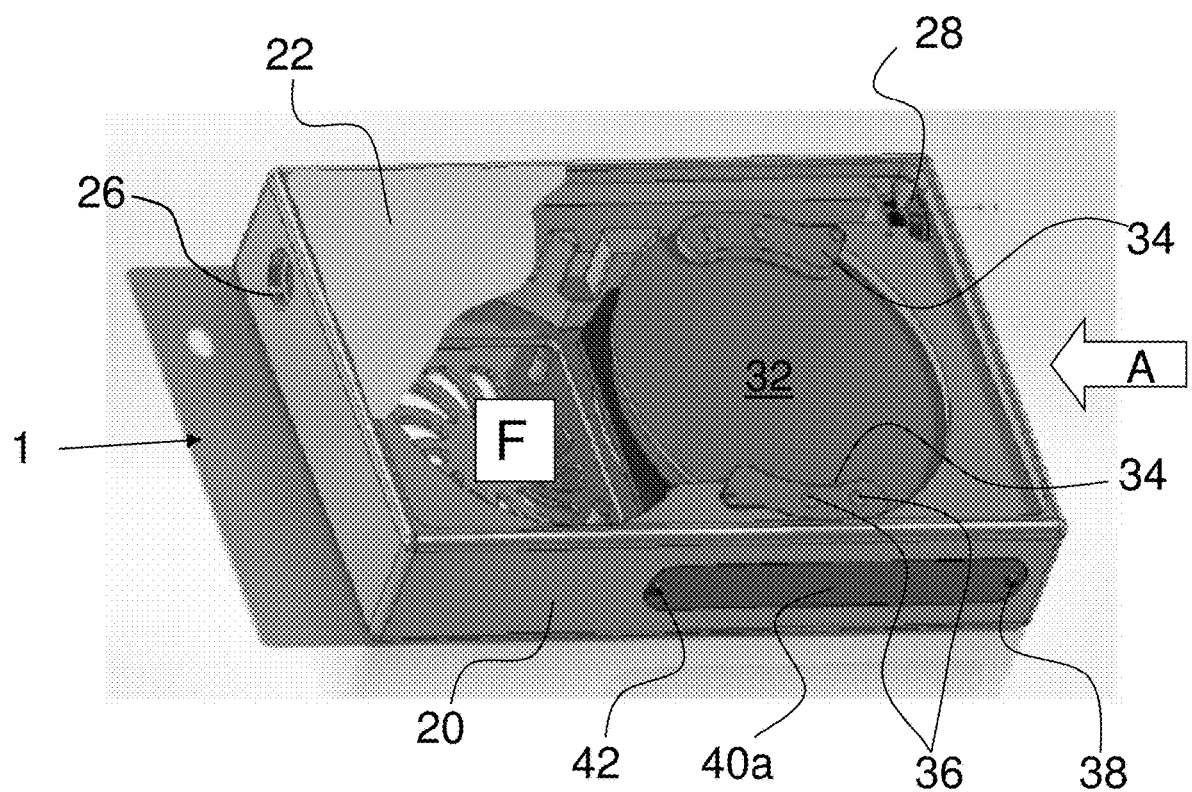
FIG. 1 is a perspective view of apparatus for the production of singlet oxygen according to the invention, with a side cover and certain internal components omitted for clarity.
Figure 2:
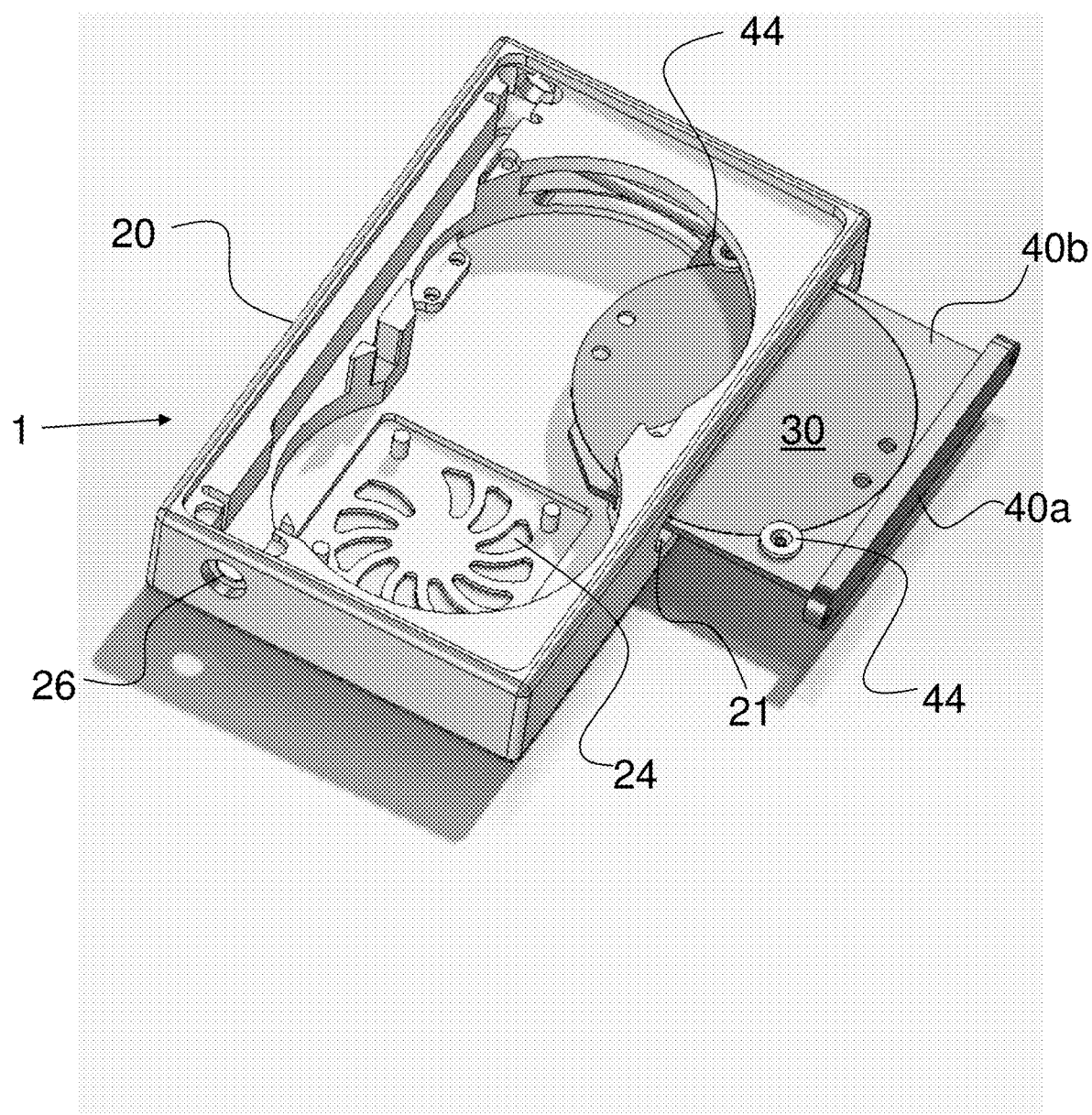
FIG. 2 shows the apparatus of FIG. 1, with a slidable carriage partially removed from the housing of the apparatus, and with all other components omitted.
Figure 3:
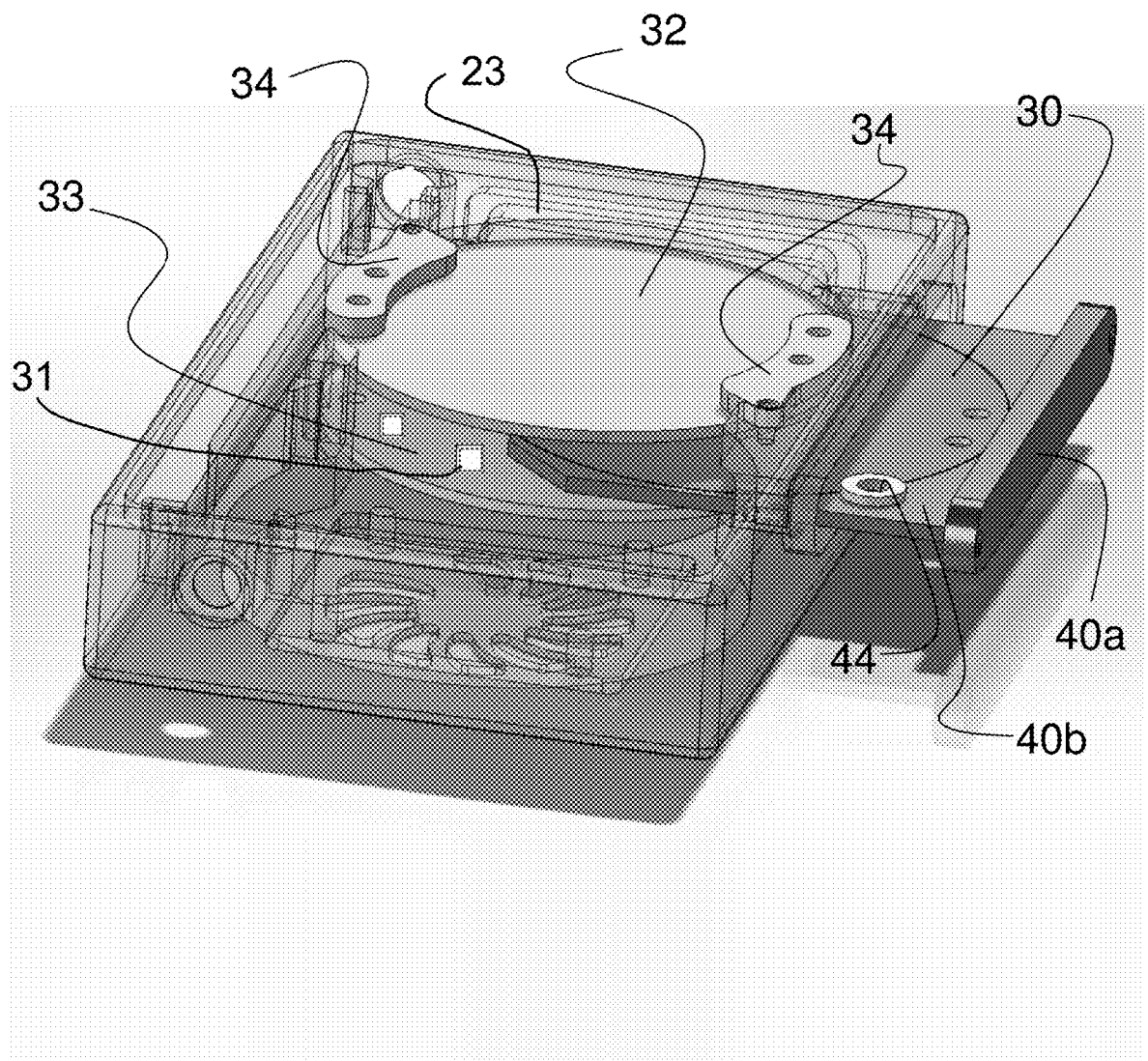
FIG. 3 is a perspective view of the apparatus of FIG. 1, showing the construction of an activating assembly, again showing the slidable carriage, which forms part of that assembly, partially removed, and with other components omitted or shown as hidden detail.

Referring first to FIG. 1, apparatus for the production of singlet oxygen is generally designated 1 and comprises a generally rectangular housing 20, the base and sides of which are integrally formed. The housing is completed by a top plate 22, which in FIG. 1 is cut away (and in FIGS. 2 and 3 is omitted altogether) to reveal internal components of the apparatus 1.

In the following, references to "right" and "left", "above" and "below", and to "upper" and "lower" refer to the orientation of the apparatus 1 in FIG. 1.

The housing 20 has an air inlet 23 (shown in FIG. 3) at its right hand end through which, in use, air is drawn along the direction of arrow A. The flow of air is created by the action of a conventional electrical fan unit, not shown in the drawings but schematically indicated by F in FIG. 1. The effect of the fan F is to draw air into the apparatus 1 along the direction of arrow A and to expel the air through openings that constitute an outlet 24 in the base of the housing 20.

The action of the fan F may alternatively be reversed, so that air flows through the apparatus in the opposite direction.

The left hand end of the housing 20 is provided with a socket 26 for a suitable power supply, which is normally a low voltage supply from a transformer connected to a domestic AC mains supply. The power supply provides the necessary power for operation of the fan F and also the light-emitting diodes that are described below. The right hand wall of the housing is also provided with an on/off switch 28, part of which is visible in FIG. 1.

An activating assembly is positioned in the path of air from the air inlet to the outlet 24.

To the extent described above, the apparatus 1 is as described in earlier International patent application WO-A-2012-056225. Where the device of the present invention differs from that previously described is primarily in the nature of the activating assembly.

The activating assembly comprises an activating disc 30, the upper and lower surfaces of which carry a fine coating of a finely-divided photosensitiser. Typically, the activating disc 30 has roughened or pitted surfaces over which the powdered photosensitiser is distributed.

The coated surfaces of the activating discs 30 are juxtaposed with upper and lower illuminating panels 32,33 that are of very similar dimensions to the activating disc 30. The lower illuminating panel 33 is fixed by screws directly to lugs formed on the base of the housing 20, and the upper illuminating panel 32 is mounted within the housing 20 by means of brackets 34 that are attached to the illuminating panel 32 and to the housing 20 by means of screws 36.

The activating disc 30 and the upper and lower illuminating panels 32,33 are mounted in fixed relation, the activating disc 30 being located substantially centrally between the upper and lower illuminating panels 32,33, with air gaps above and below the activating disc 30, through which, in use, air is drawn by the action of the fan F. The underside of the upper illuminating panel 32 carries an array of surface-mounted LEDs (not visible in the drawings), such that light from the LEDs impinges on the photosensitizer carried on the upper surface of the activating disc 30, as air passes between the activating disc 30 and the upper illuminating panel 32. Similarly, the upper surface of the lower illuminating panel 33 carries an array of LEDs 31 (shown in FIG. 3) that are directed towards the underside of the activating disc 30. The electronic components required for operation of the LEDs are mounted on the reverse sides of the upper and lower illuminating panels 32,33, i.e., the upper side of the upper illuminating panel 32 and the underside of the lower illuminating panel 33. These electronic components are omitted from the drawings, which present a somewhat schematic depiction of the illuminating panels 32,33.

Most importantly, in relation to the present invention, the activating disc 30 is mounted on a slidably removable carriage 40. The carriage 40 extends through a slot 21 (see FIG. 2) formed in a wall of the housing 20, and comprises a terminal flange 40a that is received closely within a recess in that wall that surrounds the slot 21. The carriage 40 is secured by means of screws 38, 42 engaged with the housing 20 through holes at the ends of the flange 41.

Figure 4:
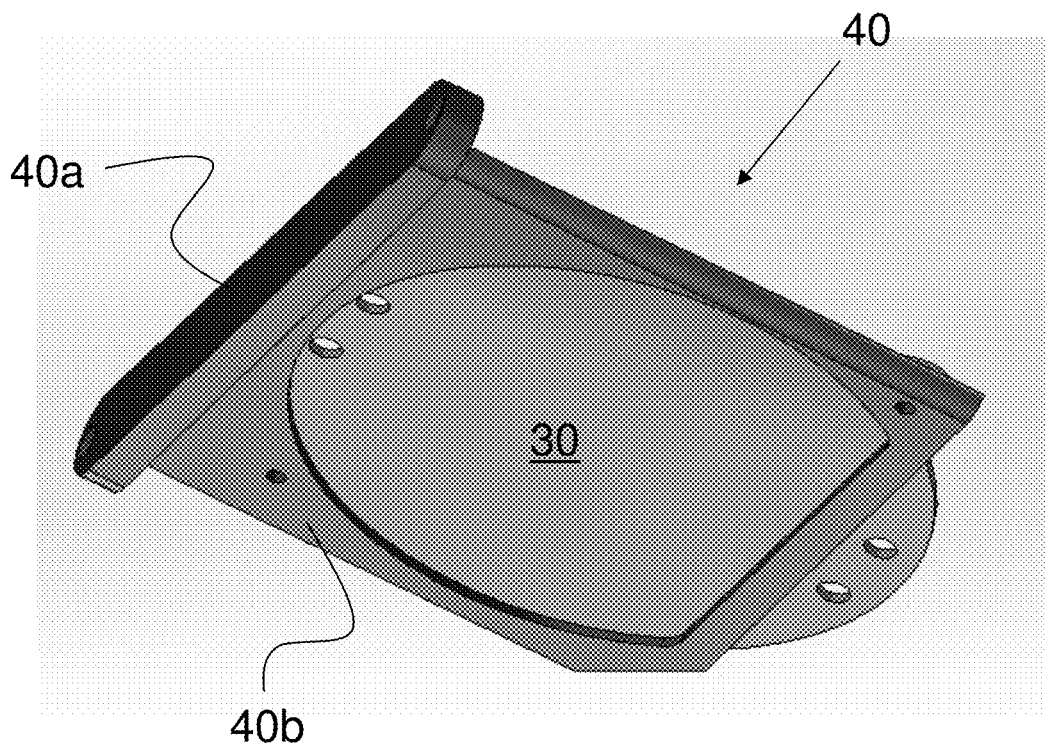
FIG. 4 is an underside perspective view of the slidable carriage that forms part of the activating assembly of the apparatus of FIG. 1.

The form of the carriage 40 is most apparent from FIGS. 2-4. As can be seen, the carriage includes a flat tray 40b with a part-circular opening that is slightly smaller in dimensions than the activating disc 30 that rests on the upper surface of the tray 40b. A recess extends around the upper edge of the opening in the tray 40b, such that the activating disc 30 sits within that recess, flush with the upper surface of the tray 40b. The activating disc 30 is held in position by means of a pair of bolts 44 that are engaged with the tray 40b and have enlarged heads that overlie the periphery of the activating disc 30.

Apart from the small area of overlap between the bolts 44 and the activating disc 30, the whole upper surface of the activating disc 30 is exposed to the LEDs carried by the upper illuminating panel 32, and as is apparent from FIG. 4 the majority of the lower surface of the activating disc 30 is exposed to the LEDs carried by the lower illuminating panel 33.

In use, the carriage 40 is fully engaged with the housing 20, so that the activating disc 30 is positioned between the upper and lower illuminating panels 32,33. With a power supply engaged, the apparatus 1 is turned on by means of the on/off switch 28. This turns on the LEDs on both the upper and lower illuminating panels 32,33, and causes the fan F to operate. Air is drawn through the apparatus 1, passing as it does so through the gaps between the upper and lower illuminating panels 32,33 and the activating disc 30. This generates singlet oxygen in the air, as is well-established. As disclosed herein, however, the air that is emitted from the device also contains gaseous nitrite that may also have a beneficial effect. The presence of nitrite is confirmed by the studies described below.

In a typical manner of use, the apparatus 1 is positioned adjacent to the user, ie the person seeking to derive a therapeutic benefit from inhalation of air emitted from the apparatus 1. The apparatus 1 may, for instance, be placed at the person's bedside, and be switched on while the person sleeps. In other instances, it may be desirable for the air emitted from the apparatus 1 to be channelled directly to the person's airway, for example by means of a flexible tube fitted at one end over the outlet of the apparatus 1 and at the other end to a facemask (or other device, such as a nasal cannula) worn by the person.

After prolonged use, the photosensitiser coated on the activating disc 30 may become less effective and will need to be replaced. An important advantage of the design according to the invention is that, by removal of the screws 38, 42, the carriage 40 can be readily removed from the apparatus 1. The activating disc 30 may then be removed from the carriage, by loosening of the bolts 44. A replacement activating disc 30 may then be positioned on the carriage 40, and secured with the bolts 44, and the carriage 40 may then be re-inserted into the apparatus 1. This operation may be carried out by the user of the apparatus 1, without the need to return the apparatus 1 to the manufacturer or to dispatch it to a remote service site, which would leave the user without the apparatus for a period of several days or more. Typically, the user may order a replacement activating disc 30 at regular intervals, for instance every three months or every six months, and insert that new activating disc 30 into apparatus 1 himself. The old activating disc 30 may be discarded or returned to the manufacturer for recycling.

Demonstration of the Presence of Nitrite in Output Air

Figure 5:
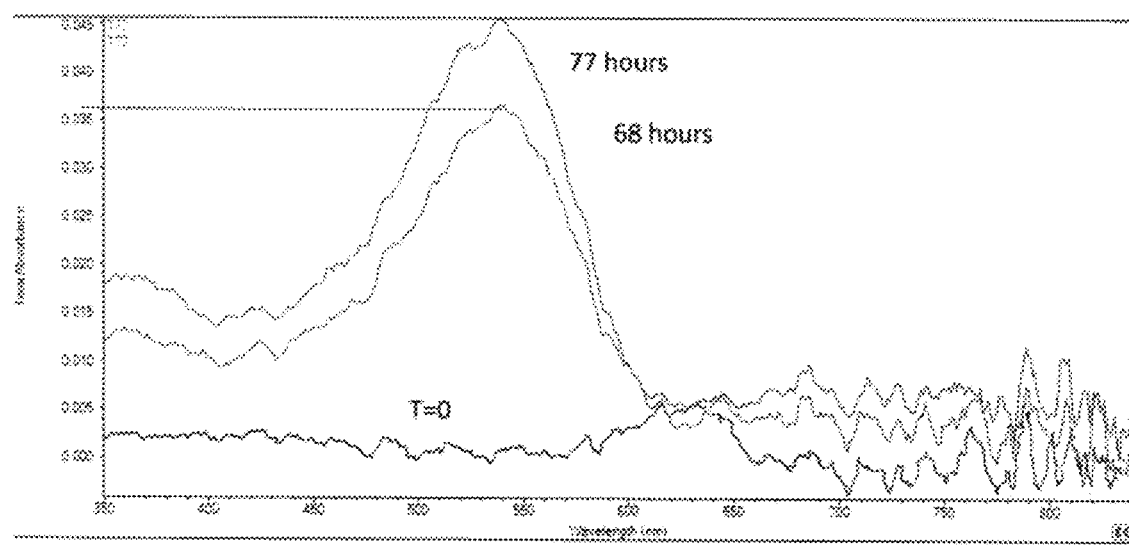
FIG. 5 is a plot of optical absorbance against wavelength for aqueous samples containing Griess reagent before, and after two prolonged periods of, passage through the samples of air from the apparatus of FIGS. 1 and 2.

Referring now to FIG. 5, an experiment to demonstrate the presence of nitrite in air that has passed through the device of FIGS. 1 and 2 was conducted as follows.

Air from the device was channelled by means of a flexible plastics tube to a vessel containing an aqueous solution containing Griess reagent. The air was bubbled through the solution for a protracted period (77 hours).

Griess reagent comprises an azo dye agent and a sulphanilamide. Nitrite ions react with the sulphanilamide to form a diazonium salt which in turn reacts with the azo dye to form a dye with a pink colour (maximum absorption at 540 nm wavelength).

FIG. 5 shows the optical absorbance of the sample prior to contact with the air from the apparatus (T=0) and after 68 hours and 77 hours of exposure to the air. The absorption peak at 540 nm that is characteristic of the product of the Griess reaction is absent initially, but has clearly developed by 68 hours and has increased at 77 hours. This is indicative of the presence of gaseous nitrite in the air bubbled through the reagent solution.

Case Studies

The following case studies relate to the effects of the apparatus of the invention (referred to as the "SoeMac") on sufferers from the specified disorders. The accounts are given in the words of the patients themselves or their parents.

Chronic Fatigue Syndrome/Myalgic Encephalopathy (ME)/Fibromyalgia

"I purchased the SoeMac almost nine weeks ago after trawling the internet for any hope of a cure for my chronic fatigue syndrome, myalgic encephalopathy (ME) and fibromyalgia.

"I found myself over 17 years ago suddenly struck down by a very high fever and couldn't get out of bed. My GP thought I had glandular fever and the following 18 months I also had CAT scans, MRI scans, brain scans, numerous blood tests and every other test you could imagine. I had endoscopies, colonoscopies, cancer tests, tests for diabetes, and every other test you could ever imagine or believe. He said after this time he had exhausted all his resources and quite frankly didn't know what to do next.

"Over the next few years I had tiny increments of work but straight home and into bed. I had to work because my illness wasn't recognised by the World Health Organisation for many years to come and I couldn't get any sickness Befits. My GP couldn't say what was wrong with me. Basically my life consisted of a little work, eating, and not much sleep. Insomnia was another symptom of my illness. I had to have a sleep study done to get me onto very high doses of sleeping medication and melatonin as my body wasn't producing melatonin itself. When that was discovered then at least I could sleep.

"I was a single woman of 34 years of age and I really had myself convinced I was dying. My GP couldn't really agree or disagree with this at this stage. I had a cleaner, gardener, and family and friends had to make all my meals. Sometimes I actually had to be fed as I couldn't hold up a fork or spoon—I simply didn't have the energy. Sometimes I could eat and at other times not a morsel would stay in my stomach.

"After the next 5 years I finally found a specialist who was able to diagnose me and I was so happy to find out at last as I thought my death was imminent. I really had myself convinced I was dying. In fact I was so ill sometimes I actually prayed for death. I was completed exhausted by this stage and found myself depressed. Then a consultant prescribed me anti-depressants. Along with the sleeping tablets life became just about bearable.

"Simple things like holding up a hair-dryer left me completely exhausted and in severe pain. Any exertion at all left me crippled with muscle pain too. Life was at this stage totally unbearable. The best way I could describe the fatigue was as if a bag of cement was tied to my ankles and wrists and absolutely any exertion became impossible.

"At that stage I had lost my job as I was unable to work for even a morning shift but I was dying inside and I really wanted to take a University course. I was always interested in psychology and although I suffered badly from brain fog I really needed something to give me hope and occupy my mind.

"I enrolled and attended as few lectures as I could get away with. Between lectures I would go outside and sleep in my car. It was a terrible time but I was so young and couldn't just give up. I drove home each day and conducted all my studying in bed. It took me a long time. I progressed over quite a few years but finally I graduated from Cambridge University with a PhD Doctorate in criminal and forensic psychology.

I found a great position and started my new career. I need to point out at this stage I was still in agony. Unfortunately after a few years I had to give in and took early retirement. I could not be at the level of my position I was in and hold it down. I could not work for weeks at a time so early retirement was my only option.

"As I was approaching my 50th birthday I was lying in bed six days out of seven, the sleeping wasn't good, couldn't shop, attend any events or had any social life at all. My bedroom became my prison again and obviously it was only going to get worse as I aged.

"By trawling the internet, I came across the SoeMac machine and came to the decision I would give it a try.

"All I can say is that it worked. I lay in bed for seven full days and nights with the SoeMac on my bedside table switched on 24 hours every day. After approximately two weeks suddenly I found I could get out of bed every day. My brain fog completely disappeared and I was "alive" for the first time in almost 18 years. My chronic fatigue went away as did all my muscle and joint pain. My "bags of cement" had completely gone. I'm up every day. If I get naturally tired I go upstairs put the SoeMac on and have a doze. When I awake I am totally alive again.

"I am adjusting after all this time to a completely new life and it does seem strange. But I am so happy and feel so healthy. After almost 19 years it's difficult to realise what a normal life actually is. But I know when I go to bed at night I fall asleep with my SoeMac and wake up 8 hours later totally refreshed and ready to face anything the day brings to me.

"I had a little setback—I found I was hyper and couldn't sleep. So I now only use the SoeMac for 4 hours every night. I feel years younger than 50 and even people whom I haven't told about the SoeMac comment on how well I am looking. My skin is better and I have been told I look years younger too. I have absolutely no effects of ME—no fatigue, no pain, no brain fog and I feel marvellous. I have a completely clear head and my memory has returned too. I can now have a normal relationship, entertain, socialise, go out shopping, and can actually cook a meal again. I look and feel years younger."

Autism Spectrum Disorder (ASD)

(a) Three-Year-Old Boy

"My son J has diagnoses of ASD and before using the SoeMac was primarily non-verbal. He had said two words prior to using, and no consistency since his regression at 13½ months.

"The first night we began using the SoeMac and implementing it into J's plan of healing (back in February) J slept through the night for 13 hours! This was huge for us as J would only sleep an average of 9 hours a night and regularly wake. He no longer wakes in the night and has continued to have a minimum 11 hours sleep. This has also then led into other huge gains in all areas:

happiness upon waking, something J never was—this was from the first night we began using huge improvement in energy levels improvements in balance and coordination better focus and attention improved eye contact—and words—We had more words in the weeks following the start of using the SoeMac. They are not consistent but we had a burst of variety near the start which is more then we have had since J's regression whatsoever."

(b) School-Age Boy

"My son is sleeping through the night since using the machine, and a lot more alert through the day. Some positive improvements, he is doing really well at school too, can't part with the machine. If I could afford it would get one for my husband too, he also feels a lot better when he had slept with it on, he recently had a heart transplant and has been left with complex needs and brain damage, he says he feels more alert and has less head-aches.

"I am using the SoeMac for my son who has autism, sensory processing disorder, non-verbal and challenging behaviour, we have used the SoeMac for a few months and we can see a difference in many areas. H my son is sleeping a lot better, he wakes up in the morning alert and happy. We have also seen more verbal words which has also helped with his challenging behaviour. Most of all he has become more alert, and his social skills are fantastic. I can say this has been all noticed since using the machine. Also H used to get up coughing and would bring up phlegm, this has also stopped. I would highly recommend this to families who have children with autism or other complex needs."

(c) Five-Year-Old Boy

"We have noticed one big significant change in B, our five year old son, who has autism, since using the SoeMac. He struggles to fall asleep and has always gone to bed late (usually around 10 pm-11 pm) so sometimes getting up for school in the morning has been a struggle, as although he was always a solid sleeper he also needed to lie-in, so was frequently tired in the morning. Since using the SoeMac he is still going to bed late but waking up 'raring to go' and much more refreshed and 'awake'. Before the SoeMac some days it could take an hour before he was 'with it' in a morning."

COPD

"This is what happened to me and how the SoeMac has changed my life.

"I joined the Coldstream Guards in 1962. When in Aden, I was blown up on an anti-tank mine with three mortar bombs under it. I suffered burns and sand-blasting to most of my body. Most explosives are poisons when exploded. They form compounds that get in your lungs and over the years my lungs have grown worse. I was awarded the George Medal, as at that time Aden was a protectorate.

"I have good knowledge of health issues, as I was a Paramedic with the London Ambulance Service for 25 years. Over the years I got worse until in 2008 I was discharged with lung and back problems. My back was just an ache, but my breathing was now very bad. I could not sleep because I could not breathe properly.

"Then a specialist diagnosed me with COPD, and from then on I went to Casualty on a regular basis. In 2013, I spent most of my time in bed as I was chronically fatigued, as I was not getting enough oxygen.

"Then I got the SoeMac, and within 5 weeks I was out of bed living a normal life. I am 74 and am now as active as when I was in the Forces, in my twenties.

"My health is now as it should be."

The invention claimed is:

1. An apparatus for producing singlet oxygen, the apparatus comprising:
   a housing having an air inlet and an air outlet;
   a fan arranged within the housing to draw air from the air inlet to the air outlet; and
   an activating unit disposed in the path of the air from the air inlet to the air outlet, wherein the activating unit includes a photosensitiser excitable by absorption of light to excite oxygen to a singlet state, and a light source arranged to illuminate the photosensitiser;
   wherein the photosensitiser is coated on a planar substrate that is mounted on a carriage that, in use, extends through an opening in the housing such that the photosensitiser is positioned within the housing in juxtaposition with the light source, and wherein the carriage is separable from the housing to remove the photosensitiser and the planar substrate from the housing while the light source remains within the housing.

2. The apparatus of claim 1, wherein the carriage comprises a tray on which the photosensitiser-coated substrate rests.

3. The apparatus of claim 2, wherein the substrate is secured to the tray.

4. The apparatus of claim 1, wherein the carriage is such that when it is inserted into the apparatus it forms part of the housing of the apparatus to form a substantially complete enclosure.

5. The apparatus of claim 1, wherein the substrate is coated on both sides with photosensitiser, and the carriage is configured such that substantially all of both major surfaces of the substrate are exposed.

6. The apparatus of claim 5, wherein the apparatus includes two illuminating panels and the carriage positions the substrate substantially centrally between those panels, so that radiation from one illuminating panel impinges on one surface of the substrate and radiation from the other illuminating panel impinges on the other surface.

7. An apparatus for producing singlet oxygen, the apparatus comprising:
   a housing having an air inlet and an air outlet;
   a fan arranged within the housing to draw air from the air inlet to the air outlet; and
   an activating unit disposed in the path of the air from the air inlet to the air outlet, wherein the activating unit includes a photosensitiser excitable by absorption of light to excite oxygen to a singlet state, and a light source arranged to illuminate the photosensitiser;
   wherein the photosensitiser is coated on a planar substrate that is mounted on a carriage having a terminal flange perpendicular to the substrate such that, when the carriage is in a closed position, the terminal flange forms a portion of an outer wall of the housing and, when the carriage is in an opened position, the carriage is separated from the housing to permit replacement of the photosensitiser.

* * * * *